United States Patent [19]

Bauer et al.

[11] 4,040,929

[45] Aug. 9, 1977

[54] OXYGEN SENSOR HAVING THIN FILM ELECTROLYTE

[75] Inventors: Carl F. Bauer, Chicago; Lawrence B. Welsh, Evanston, both of Ill.; Karl J. Youtsey, Decatur, Ala.; Frank R. Szofran, Des Plaines, Ill.

[73] Assignee: Universal Oil Products Company, Des Plaines, Ill.

[21] Appl. No.: 613,657

[22] Filed: Sept. 15, 1975

[51] Int. Cl.$^2$ .................. G01N 27/46; G01N 27/58
[52] U.S. Cl. ........................... 204/195 S; 204/192 C
[58] Field of Search ............... 204/1 S, 195 S, 192 C

[56] References Cited

U.S. PATENT DOCUMENTS

| | | | |
|---|---|---|---|
| 3,378,478 | 4/1968 | Kolodney et al. | 204/195 S |
| 3,578,578 | 5/1971 | Von Krusenstierna | 204/195 S |
| 3,619,381 | 11/1971 | Fitterer | 204/1 S |
| 3,719,576 | 3/1973 | Macur | 204/195 P |
| 3,768,259 | 10/1973 | Carnahan et al. | 60/276 |
| 3,914,169 | 10/1975 | Horowitz | 204/195 S |

Primary Examiner—G. L. Kaplan
Attorney, Agent, or Firm—James R. Hoatson, Jr.; Barry L. Clark; William H. Page, II

[57] ABSTRACT

Oxygen sensor incorporating a thin film electrolyte such as yttria stabilized zirconia sputtered onto a substrate produces an electrical signal in response to differences in oxygen partial pressures. The electrical signal changes rapidly enough for useful operation at temperatures which are substantially lower than those required by conventional oxygen sensors having a rigid, self-supporting thimble, tubular, or disc type electrolyte. For example, rapidly responding signals have been generated at temperatures below 200° C whereas state of the art devices such as those used for sensing exhaust gases in automotive vehicles require temperatures higher than about 400° C.

13 Claims, 3 Drawing Figures

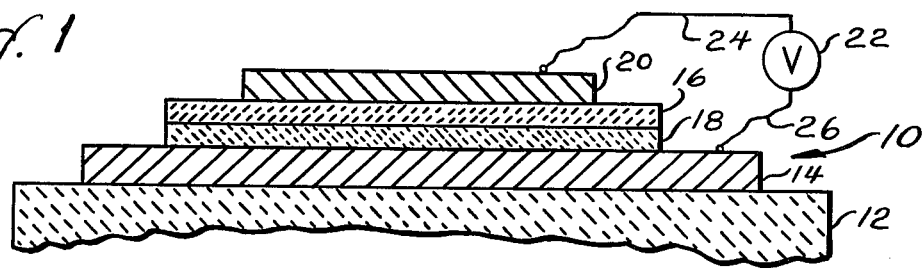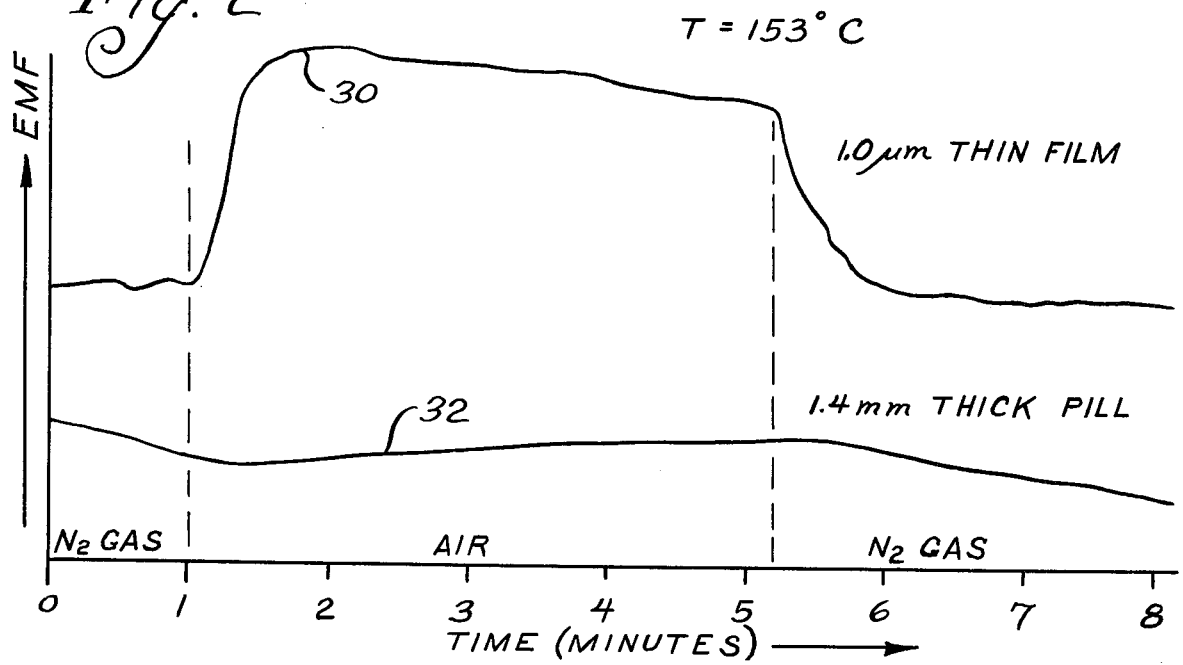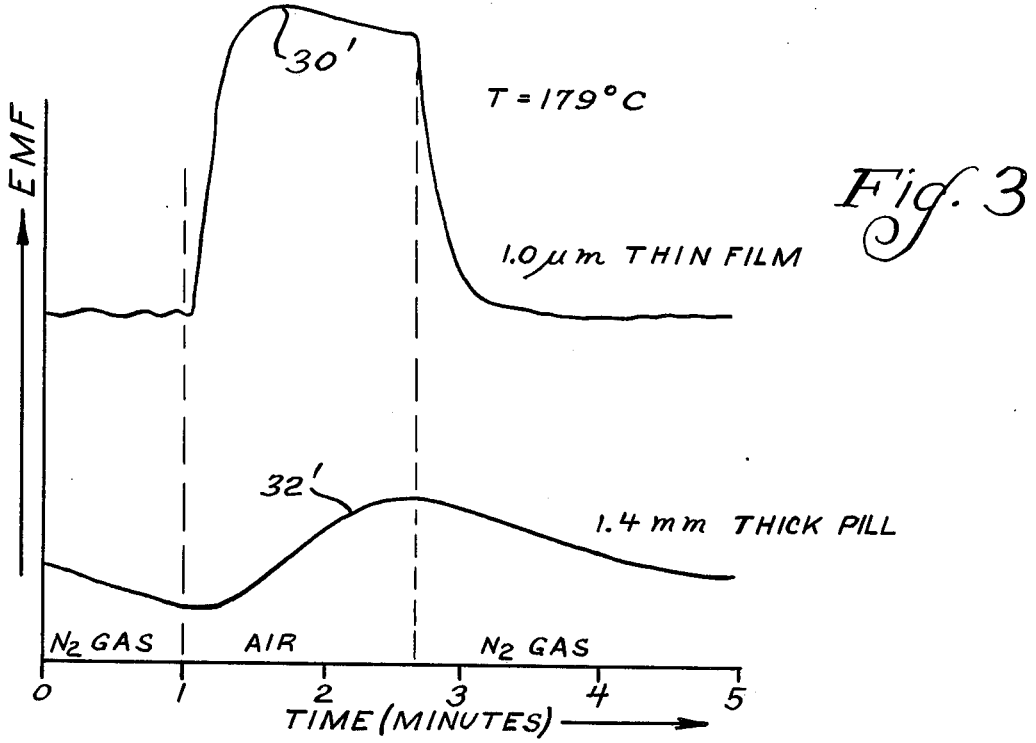

OXYGEN SENSOR HAVING THIN FILM ELECTROLYTE

The Government has rights in this invention pursuant to Contract No. F 33615-75C-2046 awarded by the Department of the Air Force.

BACKGROUND OF THE INVENTION

Oxygen sensors for generating an EMF in accordance with differences in oxygen partial pressures between a sample gas such as an automotive exhaust gas and a reference gas such as air are well known and U.S. Pat. No. 3,768,259 Carnahan, et al illustrates such a device. In such devices, two media with different partial oxygen pressures $P_{O2}'$ and $P_{O2}''$ are separated by a solid electrolyte (or ionic conductor) which has a high oxygen ion mobility. Upon attachment of conducting electrodes to both sides of the solid electrolyte, an EMF is generated which is related to the oxygen partial pressure in the two media by the Nernst equation $$EMF = \frac{t_i RT}{4F} \ln \frac{P_{O2}'}{P_{O2}''}$$

assuming oxygen can move reversibly between the media and the electrolyte. In this equation, $t_i$ is the ionic transference number, $R$ the gas constant, $T$ the absolute temperature, and $F$ is the Faraday constant. Typically, the solid electrolyte used in zirconia ($ZrO_2$) stabilized in a cubic crystal structure by calcia (CaO), magnesia (MgO), or yttria ($Y_2O_3$) in order to obtain the maximum ionic conductivity and the lowest operating temperature. Both the magnitude and temperature dependence of the solid electrolyte's ionic conductivity, $\sigma$, depend critically on the concentration of the stabilizing material. Thus, in the equation for the temperature dependence of the ionic conductivity $$\sigma = \sigma_o e^{-E_A/kT}$$

both $\sigma_o$ and the activation energy $E_a$ will depend on the concentration of the stabilizing material. For a stabilized zirconia, the best conductivity below 1000° C has been obtained with yttria at a concentration between 7 and 9 mole percent.

Existing high temperature solid electrolyte oxygen sensing devices involve the use of relatively thick (greater than 1 mm) sintered solid electrolyte materials in various configurations. Somewhat thinner sintered materials can be obtained, but only at prohibitive expense. Because the device resistance becomes very high and the time of response to a change in the oxygen partial pressure, $P_{O2}'$, becomes very long at lower temperature, for most applications, the lower temperature limit of useful operation for device using a sintered solid electrolyte is in the vicinity of 400° C.

SUMMARY OF THE INVENTION

It is among the objects of the present invention to obtain an oxygen sensor that will operate with a given response time at temperatures substantially lower than prior art devices.

Our improved sensor includes a support substrate which can be formed of a non-conducting material such as alumina, fused silica, sapphire or zirconia or of a conducting material such as stainless steel, molybdenum, or chromium, for example. Where the substrate is a non-conductor, its surface is coated with a conducting reference electrode layer such as platinum. On top of the reference electrode is a metal oxide interface region which establishes the reference oxygen partial pressure $P_{O2}''$. It is desirable that $P_{O2}''$ remain independent of operating conditions so that the EMF will change directly in accordance with changes in $P_{O2}'$. The metal oxide interface region may be composed of metals which are either the same as or different than the back electrode. In most cases the interface region will have a very low reference oxygen partial pressure $P_{O2}''$. Where the substrate is a conductor, such as stainless steel, there is no need to apply a reference electrode coating since the substrate would perform this function.

Regardless of the type of substrate used, the invention comtemplates that the solid electrolyte comprise a thin film. Preferably, the film is prepared by radio frequency (RF) sputter deposition. By the use of such a technique it is possible to obtain a device which will operate rapidly at temperatures below 200° C.

BRIEF DESCRIPTION OF THE DRAWINGS

FIG. 1 is a cross-section (not to scale) of a thin film oxygen sensor; and

FIGS. 2 and 3 are graphs plotting the voltage generated in alternate nitrogen and air atmospheres by a thin film sensor and a thick pill sensor against time for two different temperatures.

DESCRIPTION OF THE PREFERRED EMBODIMENT

Referring to FIG. 1, the side cross-section of a sensor device 10 is depicted. The sensor 10 may be made from a high quality as-fired 13 by 13mm alumina substrate 12 of the type normally used in thin film microcircuitry, a platinum coating 14 is deposited on the substrate 12 by vacuum evaporation. The platinum coating 14 is made sufficiently thick (600–1200 A) to ensure a low surface resistance (corner to corner resistance less than 10 ohms). In the RF-sputter deposition of the zirconia film 16, an oxide-platinum interface region 18 is formed which establishes an oxygen partial pressure $P_{O2}''$ of about $10^{-20\pm5}$ atm. at the back or reference electrode 14. This is in contrast to the air reference electrode used in an automotive oxygen sensor ($P_{O2}'' = 0.2$ atm).

The critical component of the device 10 is the zirconia film 16. In order to obtain the maximum low temperature ionic conductivity for the sputter deposited film we used a sintered sputtering target (not shown) of 8 mole % yttria stabilized zirconia. Adequate ionic conductivities can probably be achieved for yttria concentrations between 5 and 10 mole percent. Films 16 from 0.030 to 1.50 μm thick, depending on the quality of the substrate, are then deposited on the platinum coating 14 creating the interface region 18. The chemical composition and microstructure of the film determine the usability of the deposite film and are controlled by the various putter deposition parameters including substrate temperature, argon pressure, deposition rate, RF-bias on the substrate, and the oxygen content of the argon has (reactive sputtering). We have obtained stoichiometric zirconia films with no RF-bias using alumina substrates at room temperature, 20 mtorr argon pressure, and a deposition rate of 35 A/min in a diode RF-sputtering system. We have also obtained stoichiometric zirconia films with −40 volts RF-bias on alumina and stainless steel substrates at room temperature, 20 mtorr argon pressure, and a deposition rate of 35 A/min in the same RF-sputtering system. In both cases the oxygen content of the argon gas was that of normal purity argon. It is expected that the oxygen content of the sputtering gas can have a dramatic effect on film stoichiometry and quality and can be as high as 100% oxygen.

The metal-oxide interface region 18 is established by the sputtering parameters at the onset of film deposition. It is expected that the oxygen content, thickness, and microstructure of this region will determine both $P_{O2}''$ and the stability of device performance. We believe it is desirable that this region 18 be sufficiently thick (10–50 Å) to allow for substantial oxygen adsorption or desorption through the zirconia film 16 without altering $P_{O2}''$ while being sufficiently thin to provide adequate electrical conductivity.

The front or sensing electrode 20 must be porous to oxygen gas and preferably of high surface area to enhance the rate of adsorption and dissociation of oxygen gas in the solid electrolyte 16. Typically, this electrode is made from either a conductive platinum-containing colloid which is fired about 900° C following application, or from an application of chloroplatinic acid which is then fired about 450° C in a hydrogen atmosphere.

For EMF sensing by meter 22, lead wires 24, 26 of copper or a similar material can be attached by standard techniques to the sensing and reference electrodes 20, 14 respectively. At 100° C with the reference electrode 14 at $P_{O2}'' = 10^{-20}$ atm and an oxygen pressure of $P_{O2}' = 1$ atm at the front electrode 20, the aforementioned Nernst equation predicts a sensor voltage of 370 mV in the case where $t_i$ equals unity. A change of $P_{O2}'$ to 0.1 atm would predict a lowering of the sensor voltage by 18.5 mV. Although the predicted voltages are quite adequate for simple measurement, the degree to which they are obtainable is dependent on one's ability to achieve a $t_i$ close to unity. Favorable value of $t_i$ appear to be achievable where the electrolyte film has a dense, non-columnar structure as a result of selecting appropriate sputtering parameters. In one test sample a $t_i$ of 0.92 was achieved at a temperature of 200° C for oxygen partial pressures in the range 0.01–0.20 atm. That sample consisted of a 0.5 m thick $Y_2O_3$-doped $ZrO_2$ film which had been sputter deposited onto a stainless steel substrate. The substrate was used as the reference electrode and the sensing electrode was porous platinum which had been applied as a colloid.

The device components referred to in FIG. 1 can be modified in a large number of ways while maintaining essentially the same operational characteristics described above. The materials described above are not intended to be limiting but are presented by way of example. Substrates 12 such as quartz, polished sapphire, zirconia, etc. may be used in place of alumina. They would still be coated with the platinum layer 14 to obtain a conducting reference electrode. Metal substrates such as stainless steel, molybdenum, chromium, etc. may be used to replace both 12 and 14. With the metal substrates, the nature of the metal-oxide interface region 18 and the reference oxygen pressure $P_{O2}''$ will differ from the embodiment of the device described above. Other metallization layers 14 such as molybdenum, chromium, etc. may be used on insulating substrates which would alter the nature of the interface region 18 and the reference oxygen pressure $P_{O2}''$.

Establishing an interface region 18 capable of absorbing or desorbing a substantial quantity of oxygen without alteration of $P_{O2}''$ may be accomplished in various ways. A plurality of oxides of a metal, which may be the same as or different than the reference or back electrode 14, may be deposited by RF sputtering, evaporative technique, anodization, controlled oxidation in air or another oxygen bearing atmosphere, etc. The same purpose may be accomplished by the use of a plurality of oxides of various metals.

A number of other ionic conductors may be used to produce the solid electrolyte film 16 beside the yttria zirconia film described in the specific embodiment. Calcia or magnesia stabilized zirconias may be used as well as yttria, calcia or magnesia doped cerias, hafnias, or thorias. In addition, a number of lanthanide or bismuth oxide materials may also be satisfactory. Perhaps the next best choice to an 8 mole % yttria stabilized zirconia film would be one composed of a 5 mole % yttria doped ceria. In this case the sputter deposited film is more likely to be in the cubic fluorite structure in the as-sputter deposited form.

Another possible alternative for preparation of the electrolyte would involve sputter deposition of the solvent oxide (e.g. $ZrO_2$, $CeO_2$, etc.) followed by ion implantation of the solute cation (e.g. $Y^{3+}$, $Ca^{2+}$, etc.). It may be necessary to follow ion implantation by a thermal treatment to stabilize the solid solution for some cations. One advantage of using this technique is the "self-referencing" of the electrolyte film. That is, since the ion-implanted cation will, in general, not be implanted throughout the entire solvent oxide, but only at the upper portion, the reference oxygen pressure $P_{O2}''$ will be that of the solvent oxide. The advantage to be gained by this method fabrication is that $P_{O2}''$ is established by the oxygen pressure of the solvent oxide rather than by the narrow metal-oxide interface region 18.

Other alternative methods for preparing the electrolyte film 16 involve the anodization of the metal or alloy (YZr, Ce, CeY, etc.) to form the oxide film. Bulk metal or an alloy with an anodized surface could serve as a combination of support substrate 12, metallic coating 14, metal-oxide interface region 18 and electrolyte film 16, or the desired metal or alloy could be deposited on a substrate by vapor deposition, chemical techniques, DC or RF sputtering, etc. and anodized following deposition to form the oxide film. It may be necessary to follow anodization by a thermal treatment to obtain the desired film structure for maximum ionic conductivity.

FIGS. 2 and 3 are graphs illustrating the improvement in low temperature response of a thin film electrolyte sensor as compared to a sensor using an electrolyte in the conventional wafer or pill geometry of the type used in automotive oxygen sensors.

In FIG. 2, a 1 $\mu$m thick thin film sensor and a 1.4 mm thick pill type sensor were cycled between a nitrogen and an air atmosphere at a temperature of 153° C. As can be readily seen, the thin film sensor responded to the change in oxygen content in the atmosphere, as indicated by curve 30, much more rapidly than did the pill sensor, as indicated by curve 32. The thin film sensor responded in less than one minute whereas the pill sensor failed to come to equilibrium during the 4.3 minutes that the sensors were exposed to air. It is believed that the response time for the thin film device is faster than shown by curve 30 but the atomsphere in the testing furnace could not be changed rapidly enough to show the actual response time.

The FIG. 3 graph is similar to FIG. 2 but shows a comparison of the thin film and pill sensors at a higher temperature of 179° C. At this temperature the pill type sensor did not reach equilibrium in 1.7 minutes, as indicated by curve 32'. The pill type sensor generated a higher voltage than it did at 153° C, as expected since response time decreases with increases in temperature. However, the response time was still far inferior to the thin film sensor which produced the curve 30'.

We claim as our invention:

1. A thin film oxygen sensor comprising a substrate; a reference electrode coating on the substrate; an oxide-electrode interface region; a thin film layer of solid electrolyte having a thickness of less than about 1.5 μm; and a porous measuring electrode coating on the electrolyte; said oxide-electrode interface region being positioned between and in intimate contact with said reference electrode coating and said solid electrolyte so as to provide a stable reference oxygen partial pressure at the reference electrode.

2. The oxygen sensor of claim 1 wherein said electrolyte comprises zirconia doped with 6–10% yttria.

3. The oxygen sensor of claim 1 wherein said electrolyte has a thickness of less than about 0.5 μm.

4. The oxygen sensor of claim 1 wherein said electrolyte has a thickness of less than about 0.1 μm.

5. The oxygen sensor of claim 1 wherein said substrate is non-metallic.

6. The oxygen sensor of claim 1 wherein said oxide-electrode interface region comprises a metal oxide.

7. The oxygen sensor of claim 1 wherein said oxide-electrode interface region comprises the metal of the reference electrode.

8. The oxygen sensor of claim 1 wherein said oxide-electrode interface region comprises oxides of a plurality of metals.

9. The oxygen sensor of claim 1 wherein said oxide-electrode interface region comprises a plurality of oxides of a single metal.

10. A thin film oxygen sensor comprising a metal substrate which performs as a reference electrode; an oxide-electrode interface region; a thin film layer of solid electrolyte having a thickness of less than about 1.5 μm; and a porous measuring electrode coating on the electrolyte; said oxide-electrode interface region being positioned between and in intimate contact with said reference electrode and said solid electrolyte so as to provide a stable reference oxygen partial pressure at the reference electrode.

11. The oxygen sensor of claim 10 where said metal substrate is stainless steel.

12. The oxygen sensor of claim 10 wherein said electrolyte has a thickness of less than about 0.5 μm.

13. The oxygen sensor of claim 10 wherein said electrolyte has a thickness of less than about 0.1 μm.

* * * * *